US010368886B2

(12) United States Patent
Mahajan et al.

(10) Patent No.: US 10,368,886 B2
(45) Date of Patent: Aug. 6, 2019

(54) SURGICAL APPARATUS WITH FORCE SENSOR FOR EXTRACTION OF SUBSTANCES WITHIN THE BODY

(71) Applicants: Ajay Mahajan, North Canton, OH (US); Zahra Najafi, Akron, OH (US)

(72) Inventors: Ajay Mahajan, North Canton, OH (US); Zahra Najafi, Akron, OH (US)

(73) Assignee: The University of Akron, Akron ( * ) Notice: Subject to any disclaimer, the term of this patent is extended or adjusted under 35 U.S.C. 154(b) by 159 days.

(21) Appl. No.: 15/124,106

(22) PCT Filed: Mar. 6, 2015

(86) PCT No.: PCT/US2015/019132
§ 371 (c)(1),
(2) Date: Sep. 7, 2016

(87) PCT Pub. No.: WO2015/134846
PCT Pub. Date: Sep. 11, 2015

(65) Prior Publication Data
US 2017/0020541 A1 Jan. 26, 2017

Related U.S. Application Data

(60) Provisional application No. 61/949,290, filed on Mar. 7, 2014.

(51) Int. Cl.
*A61B 17/221* (2006.01)
*A61B 90/00* (2016.01)
*A61B 17/00* (2006.01)

(52) U.S. Cl.
CPC .......... *A61B 17/221* (2013.01); *A61B 90/03* (2016.02); *A61B 2017/00119* (2013.01); *A61B 2017/2212* (2013.01); *A61B 2090/064* (2016.02)

(58) Field of Classification Search
CPC . A61B 17/221; A61B 90/03; A61B 2090/064; A61B 2017/00119;
(Continued)

(56) References Cited

U.S. PATENT DOCUMENTS 4,721,507 A * 1/1988 Chin .................. A61B 17/3207
600/587
4,820,283 A * 4/1989 Schickling ............. A61B 17/22
600/587

(Continued)

*Primary Examiner* — Katherine M Shi
*Assistant Examiner* — Andrew P. Restaino
(74) *Attorney, Agent, or Firm* — Renner Kenner Greive Bobak Taylor & Weber

(57) ABSTRACT

A surgical apparatus for extraction of substances within a body of a human or animal includes an inner cannula, an extraction receptacle secured to the inner cannula, the extraction receptacle being adapted to grip substances to be extracted from the body; and a force sensor including a biasing member, the inner cannula operatively connected to the biasing member at an end of the inner cannula opposite the extraction receptacle, the biasing member exerting a biasing force biasing the inner cannula to pull the extraction receptacle in a direction toward the force sensor, wherein resistive forces on the extraction receptacle during extraction of a substance from the body act against the biasing force and move the biasing member.

15 Claims, 2 Drawing Sheets

(58) Field of Classification Search
CPC ........ A61B 2017/2212; A61B 17/2909; A61B 17/32056; G01L 1/04; Y10T 403/32065
USPC ........................................................ 606/127
See application file for complete search history.

(56) References Cited

U.S. PATENT DOCUMENTS

| | | | | |
|---|---|---|---|---|
| 5,944,728 | A * | 8/1999 | Bates | ................... A61B 17/221 |
| | | | | 604/264 |
| 7,935,077 | B2 | 5/2011 | Thor et al. | |
| 2006/0247663 | A1 * | 11/2006 | Schwartz | ............. A61B 17/221 |
| | | | | 606/114 |
| 2009/0030427 | A1 * | 1/2009 | Razvi | ............... A61B 17/22031 |
| | | | | 606/127 |

* cited by examiner

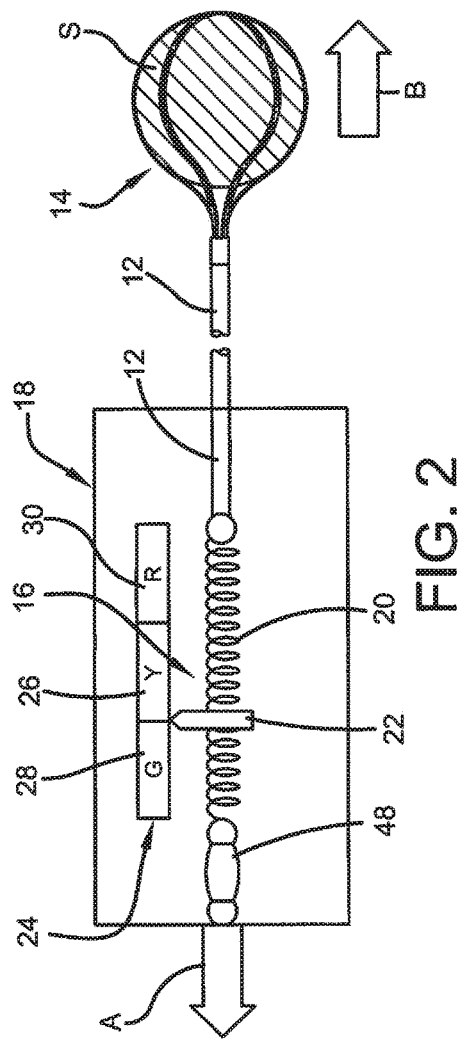
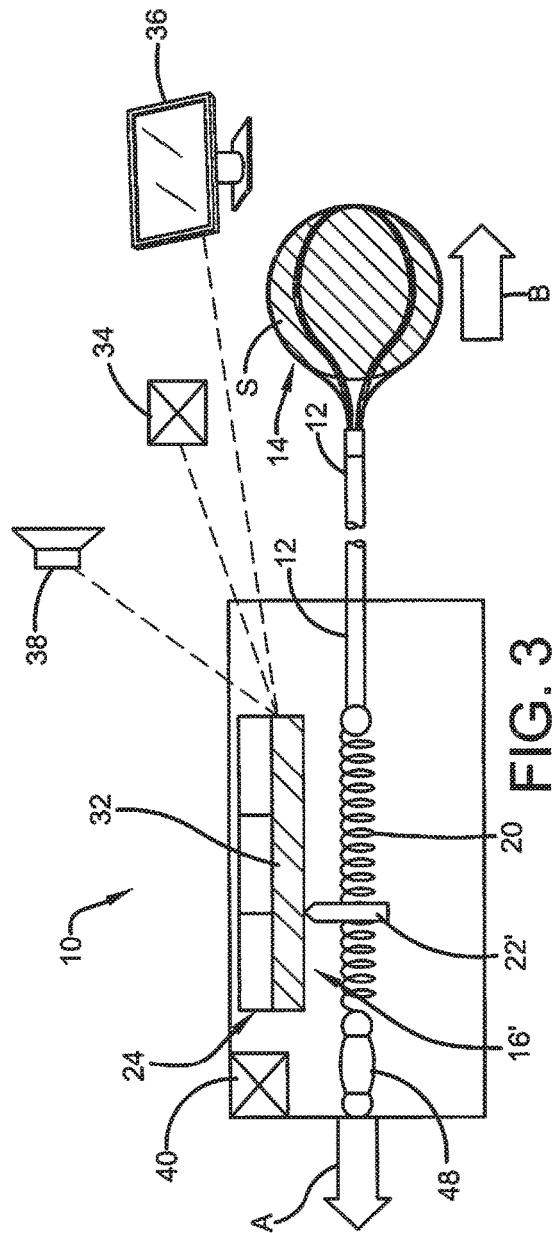

SURGICAL APPARATUS WITH FORCE SENSOR FOR EXTRACTION OF SUBSTANCES WITHIN THE BODY

CROSS-REFERENCE TO RELATED APPLICATIONS

The present application claims priority to U.S. Provisional Patent Application Ser. No. 61/949,290, filed Mar. 7, 2014, the entirety of which is incorporated herein by reference.

FIELD OF THE INVENTION

The present invention generally relates to a surgical apparatus used for extraction of substances from within the body of a human or an animal. In some embodiments, the present invention relates to surgical apparatus for the removal of kidney stones, but the concepts of the present invention are broadly applicable to other surgical apparatus for extraction of substances.

BACKGROUND OF THE INVENTION

Stone basketing has become an integral part of everyday urologic practice. Many cases will prove to be straightforward with simple stone extraction occurring in a matter of minutes. However, surgical misadventures might occur, some of which have lasting consequences. For instance, avulsion of the ureter is one of the most serious complications of ureteroscopy. It requires open or laparoscopic intervention for repair. The best way for the surgeon to avoid serious complications is to prevent them. The present invention provides devices that help the surgeon prevent such complications.

The common treatment of kidney and ureteral stones is uretroscopy. In this method once the stone is seen through the ureteroscope, a mechanical basket is used to grasp the stones and remove them. If a stone is too large to be removed, it can be fragmented into smaller pieces with laser lithotripsy, and then the smaller fragments will be removed one at a time. Stone basketing has the potential to cause ureteral injury. Hart in 1967 and Hodge in 1973, both after difficult manipulation of a ureteral stone with Dormia basket, reported the first cases of ureteral avulsion. Ureteral avulsion is one of the most feared complications of ureteroscopy, and stone extraction devices are often involved. The greatest risk factor for ureteral avulsion appears to be attempts to remove a large stone with the use of excessive force especially in a ureter with stricture (narrowing of the ureter). In addition, basketing a stone in the upper third part or section of the ureter increases the risk of avulsion because the proximal ureter has less muscle support and contains a thinner lining of mucosal cells than the distal ureter. Extraction of impacted stones can also cause ureteral avulsion or stricture formation. Furthermore, the use of multiple wire baskets has also been implicated, particularly with regard to the size of the stone (>1 cm) and the distance the stone has to cross before exiting through the ureteral meatus. The injury is typically recognized immediately because the stone is often removed along with a segment of ureter.

Perforation and urinary extravasations may also happen during stone basketing while extracting stones impacted in the collecting system wall. When a perforation occurs, the procedure should be terminated. In this situation, no attempt should be made to advance the stone basket through the perforation to retrieve the stone because these attempts will likely further enlarge the perforation. Prevention is the best way to avoid such serious complications.

It would be helpful to the surgeon to have real time access to information regarding the resistive forces encountered by the basket. Thus, if the resistive forces are too high, the surgeon can alter how the extraction is being performed. This is not only applicable to retrieval baskets for kidney stones, but is applicable to a broad range of extraction devices and procedures, as will be disclosed herein. There is a need in the art for surgical apparatus for extraction of substances from within a human or animal body, wherein the apparatus provides information regarding the resistive forces acting on the portion of the apparatus serving to extract the substance.

SUMMARY OF THE INVENTION

In a first embodiment, the present invention provides a surgical apparatus for extraction of substances within a body of a human or animal, the surgical apparatus comprising: an inner cannula; an extraction receptacle secured to the inner cannula, the extraction receptacle being adapted to grip substances to be extracted from the body; and a force sensor including a biasing member, the inner cannula operatively connected to the biasing member at an end of the inner cannula opposite the extraction receptacle, the biasing member exerting a biasing force biasing the inner cannula to pull the extraction receptacle in a direction toward the force sensor, wherein resistive forces on the extraction receptacle during extraction of a substance from the body act against the biasing force and move the biasing member.

In a second embodiment, the present invention provides a surgical apparatus for extraction of substances as in the first embodiment, further comprising an outer cannula having a distal end, the outer cannula at least partially surrounding the inner cannula, the inner cannula and the outer cannula moving axially relative to one another.

In a third embodiment, the present invention provides a surgical apparatus for extraction of substances as in either the first or second embodiment, wherein the inner cannula extends outside of the distal end of the outer cannula.

In a fourth embodiment, the present invention provides a surgical apparatus for extraction of substances as in any of the first through third embodiments, wherein the biasing member biasing the inner cannula to pull the extraction receptacle in a direction toward the distal end.

In a fifth embodiment, the present invention provides a surgical apparatus for extraction of substances as in any of the first through fourth embodiments, further comprising a handle body for gripping the surgical device.

In a sixth embodiment, the present invention provides a surgical apparatus for extraction of substances as in any of the first through fifth embodiments, wherein the handle body includes a control button manipulated to deploy the extraction receptacle.

In a seventh embodiment, the present invention provides a surgical apparatus for extraction of substances as in any of the first through sixth embodiments, wherein the control button manipulates the outer cannula to expose the extraction receptacle and to draw the extraction receptacle at least partially into the outer cannula through the distal end.

In an eighth embodiment, the present invention provides a surgical apparatus for extraction of substances as in any of the first through seventh embodiments, wherein the force sensor further includes a force indicator moving with the movement of the biasing member.

In a ninth embodiment, the present invention provides a surgical apparatus for extraction of substances as in any of the first through eighth embodiments, wherein movement of the biasing member provides notice of potential damage to the body of the human or animal.

In a tenth embodiment, the present invention provides a surgical apparatus for extraction of substances as in any of the first through ninth embodiments, wherein movement of the biasing member causes the force indicator to move into a warning region at which the surgical device provides a warning indication to the user that resistive forces are at an undesired magnitude.

In an eleventh embodiment, the present invention provides a surgical apparatus for extraction of substances as in any of the first through tenth embodiments, wherein the biasing member is selected from one of a (i) spring, (ii) elastic member or (iii) electro-magnetic/capacitive.

In a twelfth embodiment, the present invention provides a surgical apparatus for extraction of substances as in any of the first through eleventh embodiments, wherein the biasing member is an extension spring.

In a thirteenth embodiment, the present invention provides a surgical apparatus for extraction of substances as in any of the first through twelfth embodiments, wherein the warning indication is selected from either a (i) visual, (ii) auditory, or (iii) tactile response.

In a fourteenth embodiment, the present invention provides a surgical apparatus for extraction of substances as in any of the first through thirteenth embodiments, wherein the warning indication is visual, wherein the force sensor further comprises multiple positional indicia for different positions of the force indicator, with at least one of the multiple positional indicia being the warning region.

In a fifteenth embodiment, the present invention provides a surgical apparatus for extraction of substances as in any of the first through fourteenth embodiments, wherein the multiple positional indicia includes a safe region, a warning region and a damage region.

In a sixteenth embodiment, the present invention provides a surgical apparatus for extraction of substances as in any of the first through fifteenth embodiments, further comprising a monitor wherein the warning indication is visual on a screen.

In a seventeenth embodiment, the present invention provides a surgical apparatus for extraction of substances within a body having a cannula, an extraction receptacle secured to said cannula, and a handle body, as in any of the first through sixteenth embodiments, the improvement comprising the cannula being operatively connected to the handle body by a force sensor.

In an eighteenth embodiment, the present invention provides a surgical apparatus for extraction of substances as in any of the first through seventeenth embodiments, wherein the force sensor includes a biasing member.

In a nineteenth embodiment, the present invention provides a surgical apparatus for extraction of substances as in any of the first through eighteenth embodiments, wherein the biasing member is selected from one of a (i) spring, (ii) elastic member or (iii) electro-magnetic/capacitive.

In a twentieth embodiment, the present invention provides a surgical apparatus for extraction of substances as in any of the first through nineteenth embodiments, wherein the force sensor further includes a force indicator moving with the movement of the biasing member.

In a twenty-first embodiment, the present invention provides a surgical apparatus for extraction of substances as in any of the first through twentieth embodiments, wherein movement of the biasing member causes the force indicator to move into a warning region at which the surgical device provides a warning indication to the user that resistive forces are at an undesired magnitude.

In a twenty-second embodiment, the present invention provides a surgical apparatus for extraction of substances as in any of the first through twenty-first embodiments, wherein the warning indication is selected from either a (i) visual, (ii) auditory, or (iii) tactile response.

In a twenty-third embodiment, the present invention provides a surgical apparatus for extraction of substances as in any of the first through twenty-second embodiments, wherein the warning indication is visual, wherein the force sensor further comprises multiple positional indicia for different positions of the force indicator, with at least one of the multiple positional indicia indicating the potential for damage to the body.

In a twenty-fourth embodiment, the present invention provides a surgical apparatus for extraction of substances as in any of the first through twenty-third embodiments, wherein the multiple positional indicia includes a safe region, a cautionary region and an avulsion region.

BRIEF DESCRIPTION OF THE DRAWINGS

FIG. 2 is schematic representation of an embodiment of this invention in use; and FIG. 3 is a schematic representation of another embodiment of this invention in use.

DETAILED DESCRIPTION OF ILLUSTRATIVE EMBODIMENTS

Figure 1:
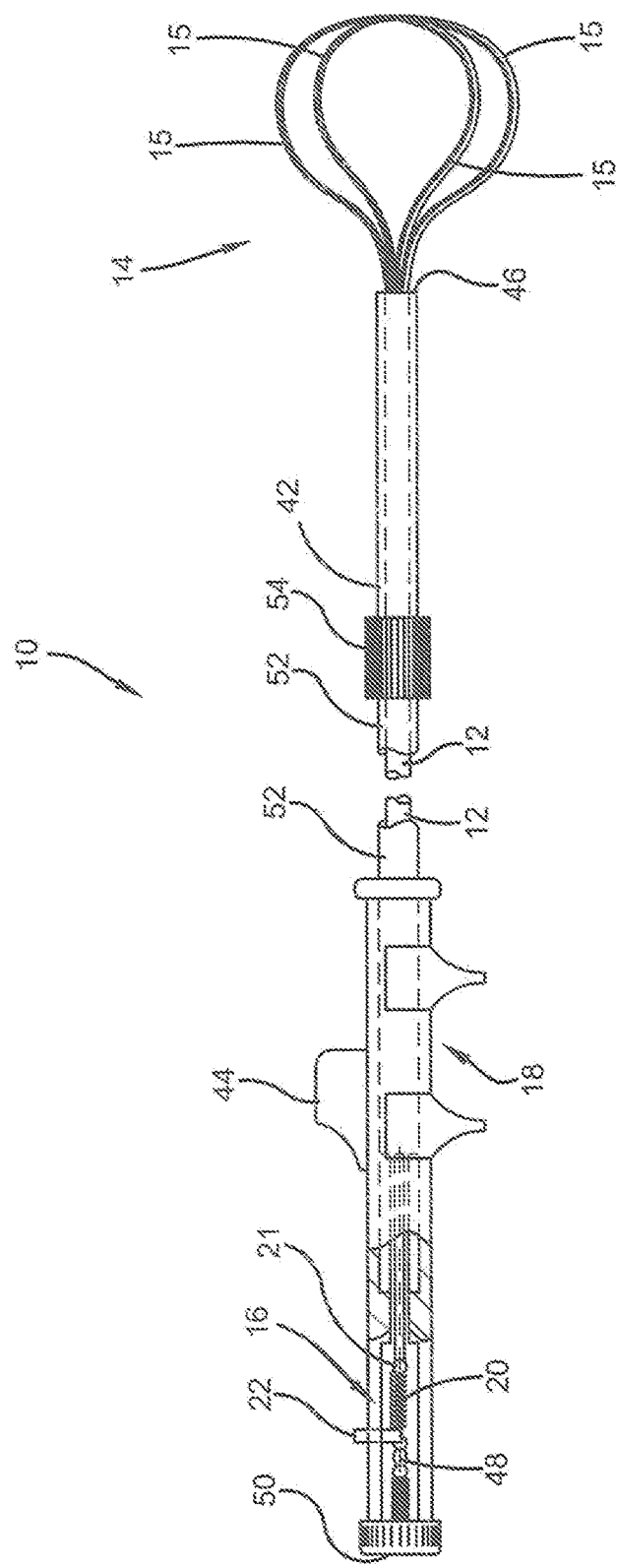
FIG. 1 is a side elevational view of an exemplary embodiment of the surgical apparatus of this invention, shown with a portion removed to better view some internal components.

With reference to FIG. 1, an embodiment of a surgical apparatus for extraction of substances within a body of a human or animal is shown and designated by the numeral 10. The surgical apparatus 10 includes an inner cannula 12, an extraction receptacle 14, a force sensor 16, and a handle body 18.

The extraction receptacle 14 is secured to the inner cannula 12 and is adapted to grip substances to be extracted from the body. In some embodiments, the extraction receptacle 14 is selected from tipless, atraumatic baskets; graspers; and screens. In some embodiments, the extraction receptacle 14 is intended to remove substances selected from kidney stones, calculi, clots, foreign bodies or the like. Various surgical apparatus employ various extraction receptacles, and the force sensor of this invention will be applicable to many of those various surgical apparatus, and the application will be readily appreciated by those of ordinary skill in the art after review of the present disclosure. This disclosure focuses on a modified version of a rigid extractor for removing kidney stones. The rigid extractor improved by this invention is similar to that found in U.S. Patent Application No. 2004/0122445.

The force sensor 16 includes a biasing member 20 and force indicator 22. In this embodiment, the force indicator 22 is shown as secured to the biasing member 20, but it will be appreciated that it could be connected to any element moving against the biasing force of the biasing member 20 as a result of the resistive forces on the extraction receptacle 14. The inner cannula 12 is operatively connected to the biasing member 20 at an end of the inner cannula 12 opposite the extraction receptacle 14. This operative connection is identified at numeral 21, and it will be appreciated that the inner cannula 12 could connect to the biasing member 20 directly or through other connective apparatus. The biasing member 20 exerts a biasing force biasing the inner cannula 12 to pull the extraction receptacle 14 in a direction toward the force sensor 16 (i.e., toward the handle body 18, leftward in the orientation of FIG. 1).

The operation of the force sensor 16 is described with reference to FIGS. 1 and 2. FIG. 2 is a schematic that helps conceptualize how the invention works by focusing on a minimal amount of elements of the apparatus 10 and their interaction. When the surgical apparatus 10 is used, and the extraction receptacle 14 is inside of the body of an animal or human and gripping a substance s to be removed therefrom, the body 18 of the apparatus 10 is pulled (leftward in FIGS. 1 and 2; arrow A) to draw the extraction receptacle 14 out of the body. Pulling the extraction receptacle 14 out of the body will be resisted by the passages of the body through which extraction receptacle 14 is being moved. These resistive forces are opposite the biasing force of the biasing member 20. Thus the resistive forces on the extraction receptacle 14 during extraction of a substance s from the body are represented at arrow B, and act against the biasing force to move the force indicator 22 in a direction opposite the direction of extraction (rightward in FIG. 1). In this embodiment, the biasing member 20 is an extension spring, and the force indicator 22 is secured to the biasing member 20 so that it moves as the spring is extended. It will be appreciated that other biasing members 20 could be employed such as elastomers, electro-magnetic transducers, capacitive transducers and the like.

The movement of the force indicator 22 provides qualitative or quantitative information regarding the magnitude of the resistive force being experienced. In some embodiments, the movement of the biasing member 20 provides a warning indication that the resistive forces are reaching the point where damage to the body may occur. In some embodiments, the warning indication is selected from a visual indication, an auditory indication, a tactile indication, and any combination of the forgoing.

In FIG. 2, the force indication is visual, and the force sensor 16 includes multiple positional indicia 24 for different positions of a visible force indicator 22. In some embodiments, the force indicator 22 is simply a pointer, or needle, as shown. The force indicator 22 is secured to the biasing member 20 to move therewith, and, as the resistive forces increase, the biasing member 20 is moved opposite the direction of its biasing force, thus also moving the force indicator 22 into different regions with different positional indicia 24. At least one of the multiple positional indicia 24 represents a warning region 26. In some embodiments, the multiple positional indicia include a safe region 28, a warning region 26, and a damage region 30. In some embodiments, the multiple positional indicia 24 are colored to provide quick visual cues as to the resistive forces being experienced. In some embodiments, the safe region 28 is colored green, the warning region 26 is colored yellow, and the damage region 30 is colored red (represented in FIG. 2 as G, Y, and R, respectively). The safe region indicates that the forces being experienced during removal are acceptably low to avoid damage to the body. The warning region 26 indicates that the resistive forces are approaching a level that can potentially result in damage, and indicates to the surgeon that he or she should proceed with caution and, if necessary, pause in the removal operation, as the pause may reduce the resistive forces and/or allow irrigation or other techniques to be employed to reduce the resistive forces. The damage region 30 is to be avoided and indicates that the body may have been damaged in light of a strong resistance to the removal of the substance s in the extraction receptacle 14.

The visual indication just described is provided by purely physical components. In other embodiments, the surgical apparatus 10 may include a force sensor that relies on a digital or analog signal to output a visual, auditory, or tactile indication, or any combination thereof. By way of example, FIG. 3 shows, a force sensor 16' having a biasing member 20 operatively secured to the inner cannula 12 and extraction receptacle 14 to be affected by the resistive forces as already disclosed. Instead of a needle or pointer, the force indicator 22' is a magnet. Instead of (or in addition to) the positional indicia 24, the force indicator 22' is moved along an axial length of a motion sensor 32 secured to the body 18 such that the force indicator 22' moves relative thereto. The movement of the magnet force indicator 22' along the motion sensor 32 generates a signal indicative of the position of the force indicator 22', and a microprocessor 34 can analyze the signal and generating any type of desired visual, auditory or tactile indication (or combination thereof) to provide warning and notice of damage. In some embodiments, the motion sensor 32 includes a plurality of discrete sensor elements that recognize the position of the force indicator 22'.

Other linear position sensors can be employed including capacitive sensors, Eddy current sensors, Inductive displacement sensors or linear variable differential transformers (LVDTs), and strain gauges.

In some embodiments, the apparatus 10 communicates with a monitor 36, for example, as represented in FIG. 3, for viewing the warning indication on a screen. This will be useful when the surgical procedure is carried out by viewing the removal of the substance on the monitor 36, providing images obtained by endoscopic cameras or like visual aids. With the surgeon watching the monitor 36, the screen or a border or other portion thereof could be caused to flash a color or otherwise provide visual cues that the resistive forces are safe, are approaching a level that will result in damage, or have entered a damage region. Red, yellow and green colors could be employed.

In some embodiments, the force indication is audible, and movement of the force indicator 22' past a warning region causes an audible signal (e.g. a beep or other distinct noise) to be made by appropriate speakers 38 to warn the surgeon. A different audible signal could be provided for safe, warning and damage regions. In some embodiments, the sound could gradually increase in intensity or pitch or some other variable noticed by the human ear to indicate in real time the increases and/or decreases in the resistive force. For example, for increasing resistive forces, the pitch would gradually go higher, while, for decreasing resistive forces, the pitch would gradually go lower.

In some embodiments, the force indication is tactile, and movement of the force indicator 22' past a warning region causes a tactile signal (e.g. slight vibration of the handle body or other distinct signal to be felt by the surgeon) to be made by appropriate vibration apparatus 40 to warn the surgeon. A different tactile signal could be provided for safe, warning and damage regions. The safe region could be characterized by no tactile signal. Suitable vibration apparatus can be based on vibration technologies for cellular phone vibration.

In some embodiments, the apparatus includes an outer cannula 42, and the inner cannula 12 and the outer cannula 42 move axially relative to one another to deploy the extraction device 14 and grip substances s therewith. Again, this invention is not limited to any particular extraction device 14.

In some embodiments as in FIG. 1, the surgical apparatus 10 further comprises a handle body 18 for gripping the surgical apparatus 10. While a particular handle body 18 is depicted in FIG. 1, other handles and configurations may be used. The handle body 18 further includes a control button 44 manipulated to deploy the extraction receptacle 14 from the outer cannula 42. In the embodiment shown, the control button 44 can manipulate the outer cannula 42 leftward in the orientation of FIG. 1 (i.e., moving the distal end 46 of the outer cannula 42 toward the handle body 18) to expose the extraction receptacle 14 at the end of the inner cannula 12. The control button 44 can manipulate the outer cannula 42 rightward in the orientation of FIG. 1 (i.e., moving the distal end away from the handle body 18) to draw the extraction receptacle 14 at least partially into the outer cannula 42 through the distal end 46. In this particular embodiment, the extraction receptacle 14 is in the form of a basket, and it will be appreciated that thee individual wires 15 of the basket expand outside of the outer cannula 42 and are necessarily drawn toward each other as the wires 15 are drawn into the outer cannula 42, thus ultimately gripping a substance s within the basket. Other extraction receptacles work in different ways but can still benefit from operative communication with a force sensor as taught herein.

In other embodiments, the control button 44 can manipulate the inner cannula 12 rightward in the orientation of FIG. 1 to expose the extraction receptacle 14 outside the outer cannula 42, and can manipulate the inner cannula 12 leftward in the orientation of FIG. 1 to draw the extraction receptacle 14 at least partially into the outer cannula 42 through the distal end 46, thus ultimately gripping a substance s within the basket. In such embodiments, movement to the right would be made against the biasing member 20 due to the fact that the extraction receptacle 14 and inner cannula 12 are operatively connected to the biasing member 20. The biasing member 20 could thus provide the leftward gripping motion for the extraction receptacle 20.

In some embodiments, the biasing member 20 is connected to a swivel 48, which is further secured to a screw 50 providing access to elements of the force sensor 16, 16', such as the biasing member 20 and/or indicator 22, 22'. In some embodiments, the outer cannula 42 is connected to a sleeve 52 by a fitting 54. Axial movement of the control button 44 (leftward and rightward in FIG. 1) causes axial movement of the sleeve 52, and also outer cannula 42 through fitting 54.

In some embodiments, the biasing member 20 may be selected from one of a (i) spring, (ii) elastic member or (iii) electro-magnetic/capacitive. In other embodiments, the biasing member is an extension spring.

In particular embodiments, the apparatus 10 is tuned to a specific procedure. First, for a given procedure, a threshold resistive force is determined, where the "threshold resistive force" is the force that should trigger a warning indication or damage indication by the apparatus. In some embodiments, both a warning threshold resistive force and a damage threshold resistive force would be determined. Such threshold resistive forces can be determined from trusted literature on the procedure of interest or from empirical study or estimates and hypotheses. With the desired threshold resistive forces determined, a suitable biasing member 20 can be chosen to allow sufficient movement of a force indicator 22 or 22' to provide a surgeon with good feel and control over the extraction procedure while also allowing for sufficient movement of the biasing member to permit visual recognition of the desired positional indicia 24 or to communicate with a motion sensor 32.

By way of example only, an experiment is conducted to determine a warning threshold resistive force and a damage threshold resistive force. An extension spring is employed as the biasing member 20. By Hookes law, the force, F, needed to extend an extension spring a distance, x, is proportional to that distance, dependent on a constant, k, characteristic of the stiffness of the extension spring. The equation is well known:

$$F = -kx.$$

With threshold forces (i.e. F values) determined by experiment, a desirable x value can be chosen based on the sensitivity of the motion sensor or the desired length and location of the positional indicia 24. If a safe region 28 of 5 mm (0.005 m) is desired, and the warning threshold resistive force is n (Newtons), the k value of desirable spring would be n/0.005. An apparatus has been built in accordance with this general method for the extraction of kidney stones. The general structure of FIG. 1 was employed, and the extension spring employed as the biasing member had the following properties: Black-Oxide steel spring with outer diameter of 0.188", inside length of 1", wire diameter of 0.022", and a rate of 2.38 lbs/inch, further including a minimum load of 0.50 lbs. and a maximum load of 2.88 lbs.

In light of the foregoing, it should be appreciated that the present invention significantly advances the art by providing a surgical apparatus for extraction of substances within the body of a human or animal that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A surgical apparatus for extraction of substances within a body of a human or animal comprising:
    an inner cannula;
    an extraction receptacle secured to said inner cannula, said extraction receptacle being adapted to grip substances to be extracted from the body;
    a force sensor including a biasing member; and
    a swivel, wherein said biasing member is connected to the swivel and wherein said inner cannula is operatively connected to said biasing member at an end of said inner cannula opposite said extraction receptacle, said biasing member exerting a biasing force biasing said inner cannula to pull said extraction receptacle in a direction toward said force sensor, wherein resistive forces on said extraction receptacle during extraction of a substance from the body act against said biasing force and move said biasing member.

2. The surgical apparatus of claim 1, further comprising an outer cannula having a distal end, said outer cannula at least partially surrounding said inner cannula, said inner cannula and said outer cannula moving axially relative to one another.

3. The surgical apparatus of claim 2, wherein said inner cannula extends outside of said distal end of said outer cannula.

4. The surgical apparatus of claim 3, said biasing member biasing said inner cannula to pull said extraction receptacle in a direction toward said distal end.

5. The surgical apparatus as in claim 4, further comprising a handle body for gripping said surgical device.

6. The surgical apparatus as in claim 5, wherein said handle body includes a control button manipulated to deploy said extraction receptacle.

7. The surgical apparatus as in claim 6, wherein said control button manipulates said outer cannula to expose said extraction receptacle and to draw said extraction receptacle at least partially into said outer cannula through said distal end.

8. The surgical apparatus as in claim 7, wherein said force sensor further includes a force indicator moving with the movement of said biasing member.

9. The surgical apparatus as in claim 8, wherein movement of said biasing member provides notice of potential damage to the body of the human or animal.

10. The surgical apparatus as in claim 9, wherein movement of said biasing member causes said force indicator to move into a warning region at which the surgical device provides a warning indication to the user that resistive forces are at an undesired magnitude.

11. The surgical apparatus as in claim 10, wherein said warning indication is selected from either a (i) visual, (ii) auditory, or (iii) tactile response.

12. The surgical apparatus as in claim 10, wherein said biasing member is an extension spring.

13. The surgical apparatus as in claim 12, wherein said warning indication is visual, wherein the force sensor further comprises multiple positional indicia for different positions of said force indicator, with at least one of said multiple positional indicia being said warning region.

14. A surgical apparatus for extraction of substances within a body, the surgical apparatus having a cannula, an extraction receptacle secured to said cannula, and a handle body, the improvement comprising said cannula being operatively connected to the handle body by a force sensor, wherein said force sensor includes a biasing member connected to a swivel and said swivel being operatively connected to said handle body.

15. The surgical apparatus as in claim 14, wherein said force sensor further includes a force indicator moving with the movement of the biasing member.

* * * * *